(12) United States Patent
Li et al.

(10) Patent No.: US 10,570,111 B2
(45) Date of Patent: Feb. 25, 2020

(54) METHOD OF PURIFYING CYCLIC ESTER

(71) Applicant: Nanjing University, Nanjing (CN)

(72) Inventors: Hong Li, Nanjing (CN); Quanxing Zhang, Nanjing (CN); Jiaye Sheng, Nanjing (CN); Na Cheng, Nanjing (CN); Wei Huang, Nanjing (CN); Wei Jiang, Nanjing (CN); Aimin Li, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 16/251,047

(22) Filed: Jan. 17, 2019

(65) Prior Publication Data

US 2019/0152939 A1    May 23, 2019

Related U.S. Application Data

(63) Continuation-in-part of application No. PCT/CN2017/100464, filed on Sep. 5, 2017.

(30) Foreign Application Priority Data

Sep. 7, 2016  (CN) .......................... 2016 1 0807374

(51) Int. Cl.
C07D 319/12    (2006.01)

(52) U.S. Cl.
CPC .................................. *C07D 319/12* (2013.01)

(58) Field of Classification Search
CPC ..................................................... C07D 319/12
See application file for complete search history.

(56) References Cited

U.S. PATENT DOCUMENTS 5,348,983 A * 9/1994 Sterzel ..................... C08J 9/141
521/54

* cited by examiner

*Primary Examiner* — Andrew D Kosar
*Assistant Examiner* — John S Kenyon
(74) *Attorney, Agent, or Firm* — Matthias Scholl P.C.; Matthias Scholl

(57) ABSTRACT

A method of purifying a cyclic ester, the method including: granulating a crude cyclic ester, an average particle size of resulting granules being 0.05-1.00 mm; adding the granules to 0-4° C. water to yield a mixture, a mass ratio of the water to the granules being (0.5-2):1; stirring the mixture, and performing solid-liquid separation on the mixture; repeating the stirring and solid-liquid separation for 1-4 times, to yield a purified cyclic ester; drying the purified cyclic ester at 0-4° C. and at an absolute pressure of less than or equal to 10 pascal for 4-6 hours, and continually drying the purified cyclic ester at 40-60° C. and at an absolute pressure of less than or equal to 5 pascal for 1-2 hours.

8 Claims, No Drawings

METHOD OF PURIFYING CYCLIC ESTER

CROSS-REFERENCE TO RELATED APPLICATIONS

This application is a continuation-in-part of International Patent Application No. PCT/CN2017/100464 with an international filing date of Sep. 5, 2017, designating the United States, now pending, and further claims foreign priority benefits to Chinese Patent Application No. 201610807374.3 filed Sep. 7, 2016. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

This disclosure relates to a method of purifying a cyclic ester.

Conventional methods for purification of crude cyclic esters, such as lactide and glycolide, include rectification, recrystallization, and washing.

Rectification is usually used in large scale production. However, it is characterized of relatively complex and costly.

Recrystallization is usually used in laboratory scale, which employs not eco-friendly organic solvents with a low yield.

Washing employs organic solvents, such as alcohols. The organic solvents are flammable and with oxygen form explosive mixtures.

SUMMARY

Disclosed is a method of purifying a cyclic ester that is efficient and eco-friendly.

The disclosure provides a method of purifying a cyclic ester, the method comprising:

(1) granulating a crude cyclic ester, an average particle size of resulting granules being 0.05-1.00 mm;

(2) adding the granules to 0-4° C. water to yield a mixture, a mass ratio of the water to the granules being (0.5-2):1; stirring the mixture, and performing solid-liquid separation on the mixture; repeating the stirring and solid-liquid separation for 1-4 times, to yield a purified cyclic ester; and (3) drying the purified cyclic ester at 0-4° C. and at an absolute pressure of less than or equal to 10 pascal for 4-6 hours, and continually drying the purified cyclic ester at 40-60° C. and at an absolute pressure of less than or equal to 5 pascal for 1-2 hours.

The purification method as described in the disclosure is a heterogeneous process, in (1), the crude cyclic ester is fully mixed with the water. In (2), the crude cyclic ester is washed repeatedly at 0-4° C. only with water as detergent. The impurities in the crude cyclic ester are extracted and separated quickly while avoiding the hydrolysis of the cyclic esters. The purified cyclic ester obtained in (2) contains a small amount of water. To avoid possible hydrolysis, the purified cyclic ester is first dried at low temperature to remove the most of residual water, and then is dried at relatively high temperature to remove trace water.

The water can be deionized water or distilled water. Studies have shown that chloride ions in common tap water can racemize chiral cyclic esters (e.g., L-lactide and D-lactide); in addition, cyclic esters, as monomers used for ring-opening polymerization, should not contain any ions which tend to affect the polymerization.

The crude cyclic ester in (1) can comprise L-lactide, or D-lactide, or glycolide.

According to the method, the purified cyclic ester can comprise 99.8 wt. % of L-lactide, and a yield of the L-lactide is greater than or equal to 98.2%; the purified cyclic ester can comprise 99.8 wt. % of D-lactide, and a yield of the D-lactide is greater than or equal to 99.1%; the purified cyclic ester can comprise 99.9 wt. % of glycolide, and a yield of the glycolide is greater than or equal to 98.8%.

Advantages of the method of purifying a cyclic ester in the disclosure are summarized as below.

1. The final product of cyclic ester contains no organic solvent with a highly purity.

2. This purification method is efficient and convenient.

3. This purification method can be applied in large scale production with an eco-friendly process.

DETAILED DESCRIPTION

To further illustrate, examples detailing a method of purifying a cyclic ester are described below. It should be noted that the following examples are intended to describe and not to limit the description.

The cyclic esters used in the following examples comprise L-lactide, D-lactide or glycolide, and the sources thereof are from one of the following aspects:

Source No. 1. Hydroxycarboxylic acids, e.g., L-lactic acid, D-lactic acid, or glycolic acid, are dehydrated and oligomerized to yield oligomeric hydroxycarboxylic acid with a weight-average molecular weight $M_w \leq 6000$. In the presence of organic guanidine compounds (e.g., creatinine, etc.), metal powders (e.g., tin, zinc, magnesium, etc.) and organic acid salts, inorganic acid salts, oxides, alkanes oxide of the metals, the oligomeric hydroxycarboxylic acid is catalyzed and depolymerized to yield crude cyclic esters.

Source No. 2. Hydroxycarboxylic acids, e.g., L-lactic acid, D-lactic acid, or glycolic acid, are dehydrated and oligomerized, and then, in the presence of organic guanidine compounds (e.g., creatinine, etc.), metal powders (e.g., tin, zinc, magnesium, etc.) and organic acid salts, inorganic acid salts, oxides, alkanes oxide of the metals, are polycondensed to yield polyhydroxycarboxylic acid. In the process, the crude cyclic esters as a by-product are produced.

Source No. 3. High purity cyclic esters in the polymer grade are ring-opening polymerized in the presence of organic guanidine compounds (e.g., creatinine, etc.), metal (e.g., tin, zinc, magnesium, etc.) powders and organic acid salts, inorganic acid salts, oxides, alkane oxides of the metals to synthesize polyhydroxycarboxylic acid. In the process, the crude cyclic esters as a by-product are produced.

Source No. 4. The prepared high purity cyclic esters are not for ring-opening polymerization and stored for more than 90 days.

The components of the aforesaid four sources of cyclic esters are listed in following Tables 1, 2, and 3.

TABLE 1

Components of crude L-lactide

| Components | Percentage (wt. %) |
|---|---|
| L-lactide | ≥90.0 |
| D-lactide | ≤1.0 |
| meso-lactide | ≤1.0 |
| Lactic acid monomers, dimers and polymers | ≤10.0 |
| Water | ≤5.0 |

TABLE 2

Components of crude D-lactide

| Components | Percentage (wt. %) |
|---|---|
| D-lactide | ≥90.0 |
| L-lactide | ≤1.0 |
| meso-lactide | ≤1.0 |
| Lactic acid monomers, dimers and polymers | ≤10.0 |
| Water | ≤5.0 |

TABLE 3

Components of crude glycolide

| Components | Percentage (wt. %) |
|---|---|
| Glycolide | ≥90.0 |
| Lactic acid monomers, dimers and polymers | ≤10.0 |
| Water | ≤5.0 |

All the four sources of cyclic esters contain impurities. To remove the impurities, the disclosure provides a method of purifying the cyclic esters.

Example 1

The crude L-lactide in this example is from Source No. 1, and the components are shown in Table 4.

TABLE 4

Comparison of purity of L-lactide before and after purification

| Components | Before purification (wt. %) | After purification (wt. %) |
|---|---|---|
| L-lactide | 95.3 | 99.8 |
| D-lactide | 0.5 | Not detected |
| meso-lactide | 1.5 | 0.2 |
| Lactic acid monomers, dimers and polymers | 1.6 | Not detected |
| Water | 1.1 | Not detected |

The method of purifying the crude L-lactide comprises:
(1) granulation: granulating 100 kg of crude L-lactide to yield granules having an average particle size of 0.10 mm;
(2) washing and separation: adding the granules of crude L-lactide in (1) to 0° C. deionized water to yield a mixture, where the mass ratio of the deionized water to the granules is 0.5:1; stirring the mixture, and performing solid-liquid separation on the mixture; repeating the stirring and solid-liquid separation for 2 times, to yield a purified L-lactide;
(3) drying: drying the purified L-lactide at 0° C. and at an absolute pressure of 5 pascal for 6 hours, and continually drying the purified L-lactide at 40° C. and at an absolute pressure of 1 pascal for 2 hours.

The yield of the resulting L-lactide is 99.0%, and the purity and components thereof are shown in Table 4.

Poly(L-lactic acid) is synthesized using the high-purity L-lactide as materials through ring-opening polymerization. The weight average weight ($M_w$) of the poly(L-lactic acid) is $5.5 \times 10^5$, the polymer dispersity index (PDI) is 1.5, and the conversion rate of the L-lactide is 100%.

Comparison Example 1

The source of crude L-lactide in this example is the same as that in Example 1, and the components are shown in Table 5.

TABLE 5

Comparison of purity of L-lactide before and after purification

| Components | Before purification (wt. %) | After purification (wt. %) |
|---|---|---|
| L-lactide | 95.3 | 99.5 |
| D-lactide | 0.5 | Not detected |
| meso-lactide | 1.5 | 0.5 |
| Lactic acid monomers, dimers and polymers | 1.6 | Not detected |
| Water | 1.1 | Not detected |

The method of purifying the crude L-lactide comprises: washing 100 kg of crude L-lactide using 1.0% sodium hydroxide aqueous solution, continuing washing the crude L-lactide using deionized water to make the mixture neutral, and drying the final product at 20° C. for 24 hours.

The yield of the resulting L-lactide is 85.0%, and the purity and components thereof are shown in Table 5.

Poly(L-lactic acid) is synthesized using the high-purity L-lactide as materials through ring-opening polymerization. The weight average weight ($M_w$) of the poly(L-lactic acid) is $1.2 \times 10^5$, the polymer dispersity index (PDI) is 2.0, and the conversion rate of the L-lactide is 98%.

Example 2

The crude L-lactide in this example is from Source No. 2, and the components are shown in Table 6.

TABLE 6

Comparison of purity of L-lactide before and after purification

| Components | Before purification (wt. %) | After purification (wt. %) |
|---|---|---|
| L-lactide | 98.6 | 99.9 |
| D-lactide | 0.1 | Not detected |
| meso-lactide | 0.2 | 0.1 |
| Lactic acid monomers, dimers and polymers | 0.9 | Not detected |
| Water | 0.2 | Not detected |

The method of purifying the crude L-lactide comprises:
(1) granulation: granulating 50 kg of crude L-lactide to yield granules having an average particle size of 1.00 mm;
(2) washing and separation: adding the granules of crude L-lactide in (1) to 2° C. distilled water to yield a mixture, where the mass ratio of the distilled water to the granules is 1:1; stirring the mixture, and performing solid-liquid separation on the mixture; repeating the stirring and solid-liquid separation for one time, to yield a purified L-lactide;
(3) drying: drying the purified L-lactide at 2° C. and at an absolute pressure of 10 pascal for 5 hours, and continually drying the purified L-lactide at 50° C. and at an absolute pressure of 3 pascal for 2 hours.

The yield of the resulting L-lactide is 99.6%, and the purity and components thereof are shown in Table 6.

Poly(L-lactic acid) is synthesized using the high-purity L-lactide as materials through ring-opening polymerization. The weight average weight ($M_w$) of the poly(L-lactic acid) is $4.5\times10^5$, the polymer dispersity index (PDI) is 1.7, and the conversion rate of the L-lactide is 99.8%.

Example 3

The crude L-lactide in this example is from Source No. 3. That is, the high purity L-lactide prepared in Example 1 is employed to synthesize poly(L-lactic acid) through ring opening polymerization in the presence of $SnOct_2$, and crude L-lactide is recycled. The components are shown in Table 7.

TABLE 7

Comparison of purity of L-lactide before and after purification

| Components | Before purification (wt. %) | After purification (wt. %) |
|---|---|---|
| L-lactide | 99.5 | 100.0 |
| D-lactide | Not detected | Not detected |
| meso-lactide | 0.2 | Not detected |
| Lactic acid monomers, dimers and polymers | 0.3 | Not detected |
| Water | Not detected | Not detected |

The method of purifying the crude L-lactide comprises:

(1) granulation: granulating 20 kg of crude L-lactide to yield granules having an average particle size of 0.05 mm;

(2) washing and separation: adding the granules of crude L-lactide in (1) to 2° C. deionized water to yield a mixture, where the mass ratio of the deionized water to the granules is 1:1; stirring the mixture, and performing solid-liquid separation on the mixture; repeating the stirring and solid-liquid separation for one time, to yield a purified L-lactide;

(3) drying: drying the purified L-lactide at 2° C. and at an absolute pressure of 10 pascal for 5 hours, and continually drying the purified L-lactide at 50° C. and at an absolute pressure of 3 pascal for 1 hour.

The yield of the resulting L-lactide is 98.5%, and the purity and components thereof are shown in Table 7.

Poly(L-lactic acid) is synthesized using the high-purity L-lactide as materials through ring-opening polymerization. The weight average weight ($M_w$) of the poly(L-lactic acid) is $4.7\times10^5$, the polymer dispersity index (PDI) is 1.6, and the conversion rate of the L-lactide is 98.0%

Example 4

The crude L-lactide in this example is from Source No. 4. That is, the high purity L-lactide prepared in Example 1 is stored in a vacuum drier for 90 days, to yield crude L-lactide. The components are shown in Table 8.

TABLE 8

Comparison of purity of L-lactide before and after purification

| Components | Before purification (wt. %) | After purification (wt. %) |
|---|---|---|
| L-lactide | 97.1 | 99.8 |
| D-lactide | 0.2 | Not detected |
| meso-lactide | 0.3 | 0.2 |
| Lactic acid monomers, dimers and polymers | 1.8 | Not detected |
| Water | 0.6 | Not detected |

The method of purifying the crude L-lactide comprises:

(1) granulation: granulating 100 kg of crude L-lactide to yield granules having an average particle size of 0.50 mm;

(2) washing and separation: adding the granules of crude L-lactide in (1) to 4° C. distilled water to yield a mixture, where the mass ratio of the distilled water to the granules is 2:1; stirring the mixture, and performing solid-liquid separation on the mixture; repeating the stirring and solid-liquid separation for 4 times, to yield a purified L-lactide;

(3) drying: drying the purified L-lactide at 4° C. and at an absolute pressure of 8 pascal for 4 hours, and continually drying the purified L-lactide at 60° C. and at an absolute pressure of 5 pascal for 1 hour.

The yield of the resulting L-lactide is 98.2%, and the purity and components thereof are shown in Table 8.

Poly(L-lactic acid) is synthesized using the high-purity L-lactide as materials through ring-opening polymerization. The weight average weight ($M_w$) of the poly(L-lactic acid) is $5.3\times10^5$, the polymer dispersity index (PDI) is 1.6, and the conversion rate of the L-lactide is 99.5%.

Example 5

The crude D-lactide in this example is from Source No. 1, and the components are shown in Table 9.

TABLE 9

Comparison of purity of D-lactide before and after purification

| Components | Before purification (wt. %) | After purification (wt. %) |
|---|---|---|
| L-lactide | 0.6 | Not detected |
| D-lactide | 95.6 | 99.8 |
| meso-lactide | 1.8 | 0.2 |
| Lactic acid monomers, dimers and polymers | 1.4 | Not detected |
| Water | 0.6 | Not detected |

The method of purifying the crude D-lactide comprises:

(1) granulation: granulating 100 kg of crude D-lactide to yield granules having an average particle size of 0.50 mm;

(2) washing and separation: adding the granules of crude D-lactide in (1) to 4° C. deionized water to yield a mixture, where the mass ratio of the deionized water to the granules is 2:1; stirring the mixture, and performing solid-liquid separation on the mixture; repeating the stirring and solid-liquid separation for 4 times, to yield a purified D-lactide;

(3) drying: drying the purified D-lactide at 4° C. and at an absolute pressure of 8 pascal for 4 hours, and continually drying the purified D-lactide at 60° C. and at an absolute pressure of 5 pascal for 1 hour.

The yield of the resulting D-lactide is 99.1%, and the purity and components thereof are shown in Table 9.

Poly(L-lactic acid) is synthesized using the high-purity D-lactide as materials through ring-opening polymerization.

The weight average weight ($M_w$) of the poly(D-lactic acid) is $5.4\times10^5$, the polymer dispersity index (PDI) is 1.7, and the conversion rate of the D-lactide is 99.7%.

Example 6

The crude glycolide in this example is from Source No. 1. That is, 70% glycolic acid aqueous solution is subject to dehydration oligomerization to yield oligoglycolic acid having a weight average molecular weight $M_w$ $5.0\times10^3$. Thereafter, organic guanidine is added, the oligoglycolic acid is depolymerized to yield white or yellowish crude glycolide. The components are shown in Table 10.

TABLE 10

Comparison of purity of glycolide before and after purification

| Components | Before purification (wt. %) | After purification (wt. %) |
| --- | --- | --- |
| Glycolide | 96.0 | 100.0 |
| Lactic acid monomers, dimers and polymers | 2.5 | Not detected |
| Water | 1.5 | Not detected |

The method of purifying the crude glycolide comprises:

(1) granulation: granulating 100 kg of crude glycolide to yield granules having an average particle size of 0.10 mm;

(2) washing and separation: adding the granules of crude glycolide in (1) to 0° C. distilled water to yield a mixture, where the mass ratio of the distilled water to the granules is 0.5:1; stirring the mixture, and performing solid-liquid separation on the mixture; repeating the stirring and solid-liquid separation for 2 times, to yield a purified glycolide;

(3) drying: drying the purified glycolide at 0° C. and at an absolute pressure of 5 pascal for 6 hours, and continually drying the purified glycolide at 40° C. and at an absolute pressure of 1 pascal for 2 hours.

The yield of the resulting glycolide is 98.8%, and the purity and components thereof are shown in Table 10.

Poly(L-lactic acid) is synthesized using the high-purity glycolide as materials through ring-opening polymerization. The weight average weight ($M_w$) of the poly(L-lactic acid) is $0.8\times10^5$, the polymer dispersity index (PDI) is 1.8, and the conversion rate of the glycolide is 100%.

It will be obvious to those skilled in the art that changes and modifications may be made, and therefore, the aim in the appended claims is to cover all such changes and modifications.

What is claimed is:

1. A method, comprising:
   granulating a crude cyclic ester, an average particle size of resulting granules being 0.05-1.00 mm;
   adding the granules to 0-4° C. water to yield a mixture, a mass ratio of the water to the granules being 0.5-2:1; stirring the mixture, and performing solid-liquid separation on the mixture; repeating the stirring and solid-liquid separation for 1-4 times, to yield a purified cyclic ester; and
   drying the purified cyclic ester at 0-4° C. and at an absolute pressure of less than or equal to 10 pascal for 4-6 hours, and continually drying the purified cyclic ester at 40-60° C. and at an absolute pressure of less than or equal to 5 pascal for 1-2 hours.

2. The method of claim 1, wherein the water is deionized water or distilled water.

3. The method of claim 1, wherein the crude cyclic ester is L-lactide.

4. The method of claim 1, wherein the crude cyclic ester is D-lactide.

5. The method of claim 1, wherein the crude cyclic ester is glycolide.

6. The method of claim 3, wherein the purified cyclic ester comprises 99.8 wt. % of L-lactide, and a yield of the L-lactide is greater than or equal to 98.2%.

7. The method of claim 4, wherein the purified cyclic ester comprises 99.8 wt. % of D-lactide, and a yield of the D-lactide is greater than or equal to 99.1%.

8. The method of claim 5, wherein the purified cyclic ester comprises 99.9 wt. % of glycolide, and a yield of the glycolide is greater than or equal to 98.8%.

* * * * *